United States Patent
Dinno

(10) Patent No.: US 7,850,999 B2
(45) Date of Patent: *Dec. 14, 2010

(54) TOPICAL COMPOSITION AND METHOD FOR THE TREATMENT AND PROPHYLAXIS OF DERMAL IRRITATIONS

(76) Inventor: Raied Dinno, 50 Autumn Rd., Weston, MA (US) 02493

( * ) Notice: Subject to any disclaimer, the term of this patent is extended or adjusted under 35 U.S.C. 154(b) by 0 days.

This patent is subject to a terminal disclaimer.

(21) Appl. No.: 12/709,794

(22) Filed: Feb. 22, 2010

(65) Prior Publication Data

US 2010/0151048 A1    Jun. 17, 2010

Related U.S. Application Data

(63) Continuation of application No. 11/827,369, filed on Jul. 11, 2007, now Pat. No. 7,666,453, which is a continuation of application No. 10/856,740, filed on May 28, 2004, now Pat. No. 7,252,846.

(51) Int. Cl.
| | | |
|---|---|---|
| *A61K 36/886* | (2006.01) | |
| *A61K 33/06* | (2006.01) | |
| *A61K 36/00* | (2006.01) | |
| *A61K 33/30* | (2006.01) | |

(52) U.S. Cl. .............. 424/774; 424/725; 424/692; 424/555; 424/641

(58) Field of Classification Search .............. None
See application file for complete search history.

(56) References Cited

U.S. PATENT DOCUMENTS

| | | | |
|---|---|---|---|
| 4,816,254 A | 3/1989 | Moss | |
| 5,834,004 A | 11/1998 | Upmeyer et al. | |
| 5,843,998 A | 12/1998 | Song et al. | |
| 5,997,889 A | 12/1999 | Durr et al. | |
| 6,019,963 A | 2/2000 | Kling et al. | |
| 6,048,549 A | 4/2000 | Nitikhunkasem et al. | |
| 6,083,529 A | 7/2000 | Manzo et al. | |
| 6,093,414 A | 7/2000 | Capelli | |
| 6,143,285 A | 11/2000 | Howard | |
| 6,368,579 B1 | 4/2002 | Barr | |
| 6,419,963 B1 | 7/2002 | Niazi | |
| 6,589,537 B2 | 7/2003 | Harbeck | |
| 6,645,506 B1 | 11/2003 | Farmer | |
| 6,667,045 B2 | 12/2003 | Dahle | |
| 6,673,374 B2 | 1/2004 | Murad | |
| 2001/0014316 A1 | 8/2001 | Harbeck | |
| 2003/0017122 A1* | 1/2003 | Vromen | 424/59 |
| 2003/0082129 A1* | 5/2003 | Buckingham et al. | 424/70.12 |

* cited by examiner

*Primary Examiner*—Patricia Leith
(74) *Attorney, Agent, or Firm*—Weingarten, Schurgin, Gagnebin & Lebovici LLP

(57) ABSTRACT

A composition and method for the prevention and therapeutic treatment of skin conditions and disorders are disclosed. The composition and method of the invention are particularly directed to the treatment and prevention of dermal irritations. These irritations include, for example, psoriasis, eczema, ichthyosis, pruritus, dryness and dermatitis, which may cause skin to crack, chap or chafe. The composition and method are particularly useful in treating and preventing diaper dermatitis. A therapeutic composition according to the invention includes an agent, which is an enzyme constituent, promoting the synthesis of collagen and the reproduction of cells, particularly skin cells. Such therapeutic agents include, for example, zinc oxide. This agent is generally nonprescription and capable of effectively preventing and treating diaper dermatitis through local or topical application. Therapeutic compositions according to the invention also include both natural and synthetic components, which aid in application, use and treatment.

17 Claims, No Drawings

TOPICAL COMPOSITION AND METHOD FOR THE TREATMENT AND PROPHYLAXIS OF DERMAL IRRITATIONS

CROSS REFERENCE TO RELATED APPLICATIONS

The present application is a continuation application of U.S. application Ser. No. 11/827,369 filed Jul. 11, 2007 and entitled "TOPICAL COMPOSITION AND METHOD FOR THE TREATMENT AND PROPHYLAXIS OF DERMAL IRRITATIONS", which is a continuation application of U.S. application Ser. No. 10/856,740 filed May 28, 2004 and entitled "TOPICAL COMPOSITION AND METHOD FOR THE TREATMENT AND PROPHYLAXIS OF DERMAL IRRITATIONS", both of which are incorporated herein by reference in their entirety.

BACKGROUND OF THE INVENTION

Skin is the largest organ of the human body. In general, human skin includes two layers, an outer layer and an underlying layer. The outer layer is known as the epidermis, and the underlying layer is referred to as the dermis. The dermis is a connective layer that is responsible for the elasticity of skin. The epidermis primarily functions to regulate secretion and body temperature, and protect against dehydration and infection. Skin aliments or disorders, however, tend to retard the functions of the epidermis, and may limit the outer layer's ability to protect the body. Moreover, skin conditions and dermal irritations are a common problem for many individuals.

Although there are numerous skin conditions known in the field of dermatology, conditions that normally affect individuals include psoriasis, eczema, dryness and dermatitis. One form of dermatitis that is particularly problematic and known to reoccur with frequency is diaper dermatitis. Diaper dermatitis or diaper rash inflames and irritates those dermal parts of the body which are generally proximate to or covered by a diaper. This inflammation and irritation may cause skin to, for example, crack, chap or chafe.

The pharmaceutical and cosmetics industries are both concerned with treating diaper rash and its effects. A number of topical products are available to consumers for this purpose. These products include creams, starches and powders.

Although generally effective to relieve the discomfort associated with diaper dermatitis, the majority of available topical products do not include nonprescription therapeutic agents for treatment and prevention. Similarly, therapeutic agents are not available in products having both organic and synthetic components, which aid in application and use as well as treatment and prevention. In addition, these products are not effective in treating or preventing other related skin conditions. Products are also not available which are easy to apply to different areas of the body. For example, a topical talc presents application problems without the use of a carrier that remains in contact with the skin. Finally, the increasing costs of such products tends to limit consumer use.

SUMMARY OF THE INVENTION

The present invention is directed to the treatment and prophylaxis of skin aliments and disorders. Particularly, the disclosed composition and method are useful in treating and preventing skin conditions and other related dermal irritations. These conditions and irritations include, for example, psoriasis, eczema, ichthyosis, pruritus, dryness and dermatitis, which may cause skin to crack, chap or chafe.

A therapeutic composition according to the invention includes a therapeutic agent, which is an enzyme constituent promoting the synthesis of collagen and the reproduction of cells, particularly skin cells. Such therapeutic agents include, for example, iron oxide, titanium oxide, manganese oxide and zinc oxide. The therapeutic composition is preferably suitable for topical application in a nonprescription form. When topically applied, the composition is effective for treating and preventing diaper dermatitis. The composition may also include an effective combination of ingredients, such as, for example, those that are organic and synthetic, which aid in application and use as well as treatment and prevention.

In addition, the invention is directed to a method for preparing or compounding the therapeutic composition. A method for applying the composition to a dermal area is also encompassed. Finally, the therapeutic composition is incorporated with an article of manufacture. This article may be a packaging material or a device.

DEFINITIONS

The terms "therapeutic composition" or "composition" generally refer to a composition of the invention. These terms may refer to any composition suitable for treating and preventing different skin conditions. Similarly, the terms may refer to any form of the composition, such as, for example, an ointment, salve, lotion or cream.

The terms "topical" or "topically" generally refer to the manner in which the preferred therapeutic composition is applied to the epidermis of the skin.

The terms "activity" or "active" generally refer to the efficacy of an ingredient or composition exhibited during application, particularly topical application. For example, one activity associated with tea tree oil is that it is a natural antiseptic.

The terms "effective combination" or "effective amount" generally refer to an amount or combination of ingredients useful in promoting at least one specific activity. For example, an effective amount or quantity of zinc oxide is active in promoting skin cell reproduction.

The terms "dermal irritation" or "dermal irritations" generally refer to a skin condition or irritation of the epidermis. Such conditions include, for example, psoriasis, eczema, dryness and dermatitis, which may cause skin to crack, chafe, chap, inflame or dry.

DETAILED DESCRIPTION OF THE INVENTION

The present invention is effective for treating and preventing a variety of skin conditions. In one embodiment, the invention is directed to a therapeutic composition including an effective combination for the treatment and prevention of dermal irritations, particularly diaper dermatitis. The ingredients of the effective combination each exhibit at least one activity, which promotes the treatment and prevention of a skin malady. For example, a moisturizer may be active as an emollient as well as a softener of the epidermis. The therapeutic composition is also suitable for topical application, although other means of application are recognized by those of ordinary skill in the art, such as, for example, a local injection.

Preferably, the therapeutic composition includes an effective combination of a therapeutic agent, an adhesive agent, an emulsifier, an antiseptic, a moisturizer, a buffering agent, an emollient, a lubricating agent, an anesthetic and a carrier. An effective combination may require that each ingredient be present in an amount or quantity suitable for the treatment and prevention of different skin conditions. The amount or quantity of each ingredient, however, may vary depending on several factors, such as, for example, the skin condition being treated.

In one embodiment, the therapeutic agent may be provided in an amount primarily effective to promote the synthesis of collagen, and the adhesive agent may be an amount primarily effective to heal opened skin. Similarly, the emulsifier may be an amount primarily effective to promote a uniform distribution, and the antiseptic may be an amount primarily effective to cleanse a dermal area. The moisturizer may also be provided in an amount primarily effective to moisturize a dermal area, and the buffering agent may be an amount primarily effective to reduce acidity. Moreover, the emollient may be an amount primarily effective to soften a dermal area, and the lubricating agent may be an amount primarily effective to lubricate a dermal area. Finally, the anesthetic may be provided in an amount primarily effective to soothe a dermal area, and the carrier may be an amount primarily effective to carry the effective combination for application, particularly topical application.

The preferred therapeutic composition may be in any form suitable for topical application. In one embodiment, the composition is an ointment. The composition may also, for example, be compounded or blended to be applied as a salve, cream or a paste. As an ointment, the composition has a consistency suitable for uniform dermal application. Additionally, the ointment may be substantially viscous to remain in contact with the skin regardless of perspiration, excess moisture or environmental conditions.

One advantage of the therapeutic composition according to the invention is that topical application is particularly convenient for treating and preventing a variety of skin conditions. The preferred therapeutic composition may be noninvasively applied directly to the skin condition regardless of the accessibility or sensitivity of a dermal area. The composition also remains in contact with the skin without the need for an additional carrier or gauze. For example, a talc or powder may not remain in contact with the skin for an entire period of use, particularly when used under severe environmental conditions.

During topical application, the therapeutic composition aids the skin in absorbing moisture and hydrating a dermal area. This activity may be promoted by hydrophilic ingredients. The composition may also include hydrophobic compounds, which prevent moisture loss. In addition, the composition of the invention may include, for example, surfactants, antiinflammatory agents, perfumes, solvents, natural oils, fruits, coloring agents, water and vitamins including, but not limited to, antioxidants. These ingredients are understood to be a suitable substitute or supplement for the preferred ingredients of the composition, such as, for example, an antiseptic.

An additional embodiment of the therapeutic composition includes an effective combination of mineral oil, zinc oxide, quaternium-18 hectorite, magnesium hydroxide, cod liver oil, gum karaya powder, propylene carbonate, tea tree oil, aloe vera and lanolin. These ingredients may each be present in an amount or quantity effective to treat and prevent different skin conditions. Similarly, the amount or quantity of these ingredients may vary depending, for example, on a specific condition or treatment.

According to the invention, an effective combination of ingredients may include about 33% by weight mineral oil, about 30% zinc oxide, about 25% quaternium-18 hectorite, about 3.0% magnesium hydroxide, about 2.5% cod liver oil, about 2.0% gum karaya powder, about 2.0% propylene carbonate, about 1.5% tea tree oil, about 0.5% aloe vera and about 0.5% lanolin. The weight percentages of these ingredients may vary based on, for example, the addition of other ingredients or the skin condition being treated.

It is preferable that the therapeutic agent of the composition be zinc oxide. Zinc oxide acts as an enzyme constituent, which promotes the synthesis of collagen and aids in the reproduction of cells. Skin cell reproduction is beneficial for replacing those cells damaged by different maladies, such as, for example, dermatitis. It is appreciated that zinc oxide also acts as a mild astringent and a barrier agent to soothe dermal irritation and protect the epidermis. Other therapeutic agents that may be used include, but are not limited to, titanium oxide, iron oxide and manganese oxide. Various combinations of these therapeutic agents may also be used. Similarly, these agents may be added to the composition in any suitable form, such as, for example, a powder.

Zinc oxide is a natural therapeutic agent, although it may also be chemically synthesized. The ease with which zinc oxide is topically applied makes the agent remarkably effective for treating and preventing skin conditions, particularly diaper dermatitis. Other conditions treatable with zinc oxide include, for example, psoriasis, eczema, ichthyosis, pruritus, dryness and dermatitis, which may cause skin to crack, chap or chafe.

The natural and synthetic ingredients according to the invention are useful in applying the composition to the epidermis as well as treating and preventing different skin aliments. Such natural ingredients may include, for example, mineral oil, cod liver oil, gum karaya powder, tea tree oil, aloe vera and lanolin. Synthetic ingredients may also include, but are not limited to, quaternium-18 hectorite, magnesium hydroxide and propylene carbonate.

Another advantage of the present invention is that the ingredients of the therapeutic composition are generally available to pharmacists and consumers. Specifically, ingredients, such as, for example, mineral oil, zinc oxide, quaternium-18 hectorite, magnesium hydroxide, cod liver oil, gum karaya powder, propylene carbonate, tea tree oil, aloe vera and lanolin may each be used in nonprescription strength.

The ingredients of the preferred composition may be pharmaceutically compounded in any suitable form. Gum karaya, for example, may be compounded as a powder or a colloidal dispersion. It is recognized that the effectiveness of treating and preventing different skin conditions may vary depending on the compounded composition form. Moreover, it will be appreciated that these ingredients may have specific activities associated with treatment and prevention. For example, aloe vera is effective in moisturizing the epidermis and it is a soothing topical anesthetic, an antiinflammatory agent and a dermal cleansing aid.

Additionally, magnesium hydroxide may protect the epidermis from acidic feces and urine as a buffer agent in the preferred composition, although it is also understood by one of ordinary skill in the art to be an effective anesthetic. Similarly, tea tree oil cleanses the epidermis by washing away urine, feces, dirt, blood or other contaminants. What is more, tea tree oil is also effective as an antiseptic and an antimicrobial agent that inhibits the growth of microorganisms, which tend to cause infection and inflammation.

Other ingredients useful in preventing inflammation and cleansing, lubricating or protecting the epidermis include, for example, cod liver oil and gum karaya powder. Cod liver oil may reduce topical inflammation as well as lubricate the skin. Similarly, gum karaya powder protects the epidermis and also acts as an adhesive to heal opened skin. Such ingredients may also promote a specific activity through different mechanisms. For example, lanolin may moisturize skin by absorbing water from the environment as well as inhibiting the loss of water through the epidermis.

The preferred ingredients according to the invention may also act in concert to improve their efficacy for different activities. Propylene carbonate and quaternium-18 hectorite, for example, may both act together as an emollient or emulsifier. These ingredients may also be concurrently effective as an emollient and an emulsifier.

Generally, the preferred composition is topically delivered to the epidermis through a carrier. A common carrier is mineral oil, which is also presumed to promote the activities of other ingredients. Alternatively, a different carrier may be therapeutically inert or a fabric article. These different carriers may include, for example, talcs, water, gauzes or sucrose.

An alternate embodiment of the composition may also include an antifungal agent. Such agents are effective for treating fungal and yeast related infections. Topical antifungal agents may be available without a prescription, although serious infections generally require a prescribed agent. A prescription may also be required depending on the condition or patient being treated. According to the invention, it is preferred that an antifungal agent be compounded or blended with the therapeutic composition as an ointment or cream. Suitable antifungal agents include, but are not limited to, amphotericin B, butoconazole, clotrimazole, fluconazole, miconazole, ketoconazole, flucytosine, terbinafine, itraconazole and terconazole.

The therapeutic composition of the invention is prepared without difficulty from standard pharmaceutical compounding methods. One of ordinary skill in the art will appreciate the variety of compounding methods that may be used for formulation. These compounding methods allow the composition to be prepared for a particular consumer suffering from a specific condition. Moreover, these methods allow formulation changes based on the severity of the skin condition being treated. In one embodiment, the method is directed to compounding an effective combination of ingredients including, but not limited to, mineral oil, zinc oxide, quaternium-18 hectorite, magnesium hydroxide, cod liver oil, gum karaya powder, propylene carbonate, tea tree oil, aloe vera and lanolin.

Different pharmaceutical compounding methods may yield specific forms of the preferred composition. The therapeutic composition may be compounded into, for example, a solution, suspension, gel, cream, ointment, lotion or stick. Compounding may also involve blending the ingredients into a particular form suitable for topical application or other delivery methods.

One embodiment of the invention is directed to a method for treating and preventing skin aliments, particularly diaper dermatitis. The method includes providing the preferred therapeutic composition and applying it in an amount or quantity sufficient to cover a dermal area experiencing irritation. The method may also include spreading the composition topically onto the irritated area and reapplying it to provide for a uniform distribution. It will be appreciated that the composition may be applied as often or as long as required for proper treatment. Although this method is specific to topical application, numerous other delivery methods are contemplated, such as, for example, transdermally.

The invention is also directed to an article of manufacture including a packaging material for containing the preferred composition. The packaging material may comprise a label with instructions for use of the therapeutic composition. Similarly, in another embodiment, the article of manufacture may be a device incorporating the composition. Moreover, the device may be used to deliver an effective amount of the composition to a dermal area. Examples of such devices include medical devices, undergarments, implants, hypodermics or hygiene related devices.

The examples herein are presented to illustrate other advantages of the present invention and to assist one of ordinary skill in the art in making and using the preferred therapeutic composition. These examples are not intended in any way to otherwise limit the scope of the disclosure.

EXAMPLE I

According to the present invention, a therapeutic composition that is effective for treating and preventing a variety of skin conditions is prepared as follows:

| Composition Ingredients | Weight Percentages |
| --- | --- |
| Mineral Oil | About 1.0% To About 50% |
| Zinc Oxide | About 1.0% To About 50% |
| Quaternium-18 Hectorite | About 1.0% To About 50% |
| Magnesium Hydroxide | About 0.01% To About 25% |
| Cod Liver Oil | About 0.01% To About 25% |
| Gum Karaya Powder | About 0.01% To About 25% |
| Propylene Carbonate | About 0.01% To About 25% |
| Tea Tree Oil | About 0.01% To About 25% |
| Aloe Vera | About 0.01% To About 25% |
| Lanolin | About 0.01% To About 25% |

This composition may be, for example, pharmaceutically compounded, blended or both such that its consistency and form are that of an ointment.

EXAMPLE II

A therapeutic composition of the present invention, which is effective for treating and preventing a variety of skin conditions, is prepared as follows:

| Composition Ingredients | Weight Percentages |
| --- | --- |
| Mineral Oil | About 33% |
| Zinc Oxide | About 30% |
| Quaternium-18 Hectorite | About 25% |
| Magnesium Hydroxide | About 3.0% |
| Cod Liver Oil | About 2.5% |
| Gum Karaya Powder | About 2.0% |
| Propylene Carbonate | About 2.0% |
| Tea Tree Oil | About 1.5% |
| Aloe Vera | About 0.5% |
| Lanolin | About 0.5% |

This composition may be, for example, pharmaceutically compounded, blended or both such that its consistency and form are that of an ointment.

EXAMPLE III

The therapeutic composition according to the invention was used to treat an infant suffering from diaper dermatitis. The infant was known to experience a reoccurrence of diaper dermatitis approximately every week. Topical application of the composition for one day appeared to be effective in treating and preventing the diaper dermatitis, as well as the inflammation and irritation associated with the condition.

EXAMPLE IV

A preferred therapeutic composition was administered to an infant suffering from diaper dermatitis. The infant was known to experience a reoccurrence of diaper dermatitis approximately every two months. Topical application of the composition for five days appeared to be effective in treating and preventing the condition, as well as the associated inflammation and irritation.

EXAMPLE V

A preferred therapeutic composition was administered to an infant suffering from diaper dermatitis. The infant was known to experience a reoccurrence of diaper dermatitis approximately every month. Topical application of the composition for one day appeared to be effective in treating and preventing the condition, as well as the associated inflammation and irritation.

EXAMPLE VI

A preferred therapeutic composition was administered to an infant suffering from diaper dermatitis. The infant was known to experience a reoccurrence of diaper dermatitis approximately every year. Topical application of the composition for one day appeared to be effective in treating and preventing the condition, as well as the associated inflammation and irritation.

EXAMPLE VII

A preferred therapeutic composition was administered to an infant suffering from diaper dermatitis. The infant was known to experience a reoccurrence of diaper dermatitis approximately every month. Topical application of the composition for two days appeared to be effective in treating and preventing the condition, as well as the associated inflammation and irritation.

While the present invention has been described in conjunction with a preferred embodiment, one of ordinary skill, after reading the foregoing specification, will be able to effect various changes, substitutions or equivalents, and other alterations to the compositions and methods set forth herein. It is therefore intended that the protection granted by Letters Patent hereon be limited only by the definitions contained in the appended claims and equivalents thereof.

What is claimed is:

1. A method for the treatment or prevention of dermatitis, the method comprising the step of applying a composition topically to the skin of a subject having dermatitis, the composition applied in an amount sufficient to cover the area of skin impacted by dermatitis or subject to developing dermatitis; wherein the composition consists essentially of mineral oil, zinc oxide, quaternium-18 hectorite, magnesium hydroxide, cod liver oil, gum karaya powder, propylene carbonate, tea tree oil, aloe vera and lanolin.

2. The method of claim 1, wherein the composition consists essentially of:
   from about 1.0% to about 50% by weight mineral oil;
   from about 1.0% to about 50% by weight zinc oxide;
   from about 1.0% to about 50% by weight quaternium-18 hectorite;
   from about 0.01% to about 25% by weight magnesium hydroxide;
   from about 0.01% to about 25% by weight cod liver oil;
   from about 0.01% to about 25% by weight gum karaya powder;
   from about 0.01% to about 25% by weight propylene carbonate;
   from about 0.01% to about 25% by weight tea tree oil;
   from about 0.01% to about 25% by weight aloe vera; and
   from about 0.01% to about 25% by weight lanolin.

3. The method of claim 1, wherein the composition consists essentially of:
   about 33% by weight mineral oil;
   about 30% by weight zinc oxide;
   about 25% by weight quaternium-18 hectorite;
   about 3% by weight magnesium hydroxide;
   about 2.5% by weight cod liver oil;
   about 2.0% by weight gum karaya powder;
   about 2.0% by weight propylene carbonate;
   about 1.5% by weight tea tree oil;
   about 0.5% by weight aloe vera; and
   about 0.5% by weight lanolin.

4. The method of claim 1, wherein the dermatitis is accompanied by psoriasis, eczema, ichthyosis, pruritus, or skin dryness.

5. The method of claim 1, wherein the dermatitis is accompanied by microbial infection.

6. The method of claim 1, wherein the dermatitis is diaper dermatitis.

7. A method for the treatment or prevention of dermatitis, the method comprising the step of applying a composition topically to the skin of a subject having dermatitis, the composition applied in an amount sufficient to cover the area of skin impacted by dermatitis or subject to developing dermatitis; wherein the composition consists of mineral oil, zinc oxide, gum karaya powder, tea tree oil, aloe vera, and an antifungal agent selected from the group consisting of amphotericin B, butoconazole, clotrimazole, fluconazole, miconazole, ketoconazole, flucytosine, terbinafine, itraconazole, and terconazole.

8. The method of claim 7, wherein the composition consists of:
   from about 1.0% to about 50% by weight mineral oil;
   from about 1.0% to about 50% by weight zinc oxide;
   from about 0.01% to about 25% by weight gum karaya powder;
   from about 0.01% to about 25% by weight tea tree oil;
   from about 0.01% to about 25% by weight aloe vera, and
   an antifungal agent selected from the group consisting of amphotericin B, butoconazole, clotrimazole, fluconazole, miconazole, ketoconazole, flucytosine, terbinafine, itraconazole, and terconazole.

9. The method of claim 8, wherein mineral oil is from about 20% to about 40% by weight.

10. The method of claim 8, wherein zinc oxide is from about 20% to about 40% by weight.

11. The method of claim 8, wherein gum karaya powder is from about 1.0% to about 10% by weight.

12. The method of claim 8, wherein tea tree oil is from about 0.1% to about 5.0% by weight.

13. The method of claim 8, wherein aloe vera is from about 0.1% to about 5.0% by weight.

14. The method of claim 7, wherein the dermatitis is accompanied by psoriasis, eczema, ichthyosis, pruritus, or skin dryness.

15. The method of claim 7, wherein the dermatitis is accompanied by microbial infection.

16. The method of claim 7, wherein the dermatitis is diaper dermatitis.

17. A method for the treatment or prevention of dermatitis, the method comprising the step of applying a composition topically to the skin of a subject having dermatitis, the composition applied in an amount sufficient to cover the area of skin impacted by dermatitis or subject to developing dermatitis; wherein the composition consists of mineral oil, zinc oxide, gum karaya powder, tea tree oil, aloe vera, an antifungal agent selected from the group consisting of amphotericin B, butoconazole, clotrimazole, fluconazole, miconazole, ketoconazole, flucytosine, terbinafine, itraconazole, and terconazole, and an agent selected from quaternium-18 hectorite, magnesium hydroxide, cod liver oil, propylene carbonate, lanolin and combinations thereof.

\* \* \* \* \*

UNITED STATES PATENT AND TRADEMARK OFFICE
CERTIFICATE OF CORRECTION

| | |
|---|---|
| PATENT NO. | : 7,850,999 B2 |
| APPLICATION NO. | : 12/709794 |
| DATED | : December 14, 2010 |
| INVENTOR(S) | : Raied Dinno |

It is certified that error appears in the above-identified patent and that said Letters Patent is hereby corrected as shown below:

Column 3, line 50, "antiinflammatory" should read --anti-inflammatory--; and

Column 4, line 51, "antiinflammatory" should read --anti-inflammatory--.

Signed and Sealed this
Twenty-seventh Day of December, 2011

David J. Kappos
*Director of the United States Patent and Trademark Office*